US011798662B2

(12) United States Patent
Cumming et al.

(10) Patent No.: US 11,798,662 B2
(45) Date of Patent: Oct. 24, 2023

(54) METHODS FOR IDENTIFYING BIOLOGICAL MATERIAL BY MICROSCOPY

(71) Applicant: VERDICT HOLDINGS PTY LTD, Mornington (AU)

(72) Inventors: Alistair Cumming, Mornington (AU); Luan Duong Minh Lam, Hawthorn (AU); Christopher McCarthy, Hawthorn (AU); Michelle Dunn, Hawthorn (AU); Luke Gavin, Hawthorn (AU); Samar Kattan, Hawthorn (AU); Antony Tang, Hawthorn (AU)

(73) Assignee: VERDICT HOLDINGS PTY LTD, Mornington (AU)

( * ) Notice: Subject to any disclaimer, the term of this patent is extended or adjusted under 35 U.S.C. 154(b) by 0 days.

(21) Appl. No.: 16/978,000

(22) PCT Filed: Mar. 5, 2019

(86) PCT No.: PCT/AU2019/050184
§ 371 (c)(1),
(2) Date: Sep. 3, 2020

(87) PCT Pub. No.: WO2019/169432
PCT Pub. Date: Sep. 12, 2019

(65) Prior Publication Data
US 2021/0248419 A1    Aug. 12, 2021

(30) Foreign Application Priority Data

Mar. 7, 2018 (AU) ................................ 2018900739

(51) Int. Cl.
*G06T 7/00* (2017.01)
*G16H 10/40* (2018.01)
(Continued)

(52) U.S. Cl.
CPC .............. *G16H 10/40* (2018.01); *G06F 16/51* (2019.01); *G06F 18/2148* (2023.01);
(Continued)

(58) Field of Classification Search
CPC .... G06K 9/6257; G06K 9/6253; G06F 16/51; G06T 7/0012; G06T 7/11; G06T 7/194;
(Continued)

(56) References Cited

U.S. PATENT DOCUMENTS 10,467,754 B1 * 11/2019 Ando ................... G06V 20/698
2005/0262031 A1   11/2005 Said et al.
(Continued)

FOREIGN PATENT DOCUMENTS

WO       2016160491 A1    10/2016
WO       2017201540 A1    11/2017

OTHER PUBLICATIONS

International Search Report dated Jun. 14, 2019 for Corresponding International Patent Application PCT/AU2019/050184 Filed on Mar. 5, 2019.
(Continued)

*Primary Examiner* — Wesley J Tucker
*Assistant Examiner* — Han Hoang
(74) *Attorney, Agent, or Firm* — David D. Brush; Westman, Champlin & Koehler, P.A

(57) ABSTRACT

The present invention relates generally to the field of computer-based image recognition. More particularly, the invention relates to methods and systems for the identification, and optionally the quantitation of, discrete objects of biological origin such as cells, cytoplasmic structures, parasites, parasite ova, and the like which are typically the subject of microscopic analysis. The invention may be embodied in the form of a method for training a computer to identify a target biological material in a sample. The method may include (Continued)

accessing a plurality of training images, the training images being obtained by light microscopy of one or more samples containing a target biological material and optionally a non-target biological material. The training images are cropped by a human or a computer to produce cropped images, each of which shows predominantly the target biological material. A human then identifies the target biological material in each of the cropped images where identification is possible, and associating an identification label with each of the cropped images where identification was possible. A computer-implemented feature extraction method is then applied to each labelled cropped image. A computer-implemented learning method is then applied to each labelled cropped image to associate extracted features of abiological material with a target biological material.

10 Claims, 8 Drawing Sheets

(51) Int. Cl.
    G06T 7/194    (2017.01)
    G06T 7/11     (2017.01)
    G06T 7/73     (2017.01)
    G16H 30/40    (2018.01)
    G06F 16/51    (2019.01)
    G06V 20/69    (2022.01)
    G06F 18/214   (2023.01)
    G06F 18/40    (2023.01)
    G06V 10/94    (2022.01)
    G06N 20/00    (2019.01)

(52) U.S. Cl.
    CPC ............ *G06F 18/40* (2023.01); *G06T 7/0012* (2013.01); *G06T 7/11* (2017.01); *G06T 7/194* (2017.01); *G06T 7/73* (2017.01); *G06V 10/945* (2022.01); *G06V 20/695* (2022.01); *G06V 20/698* (2022.01); *G16H 30/40* (2018.01); *G06N 20/00* (2019.01); *G06T 2207/10056* (2013.01); *G06T 2207/20021* (2013.01); *G06T 2207/20081* (2013.01); *G06T 2207/20092* (2013.01); *G06T 2207/20132* (2013.01); *G06T 2207/30004* (2013.01)

(58) Field of Classification Search
    CPC ............ G06T 7/73; G06T 2207/10056; G06T 2207/20021; G06T 2207/20081; G06T 2207/20092; G06T 2207/20132; G06T 2207/30004; G06T 2207/20104; G06V 10/40; G06V 10/758; G06V 20/695; G06V 20/698; G16H 10/40; G16H 30/40; G16H 50/20; G16H 30/20; G06N 20/00; G06N 20/10; G06N 3/0454; G06N 3/08; G16B 35/00
    See application file for complete search history.

(56) References Cited

U.S. PATENT DOCUMENTS

2008/0082468 A1* 4/2008 Long ............... G06K 9/6269
                                                    706/12
2019/0065817 A1* 2/2019 Mesmakhosroshahi ...............
                                                 G06F 18/2148
2020/0372235 A1* 11/2020 Peng ................ G01N 1/30

OTHER PUBLICATIONS

Written Opinion dated Jun. 14, 2019 For Corres{Ondinginternational Patent Application PCT/AU2019/050184 Filed on Mar. 5, 2019.

* cited by examiner

METHODS FOR IDENTIFYING BIOLOGICAL MATERIAL BY MICROSCOPY

The present application is a Section 371 National Stage Application of International Application No. PCT/AU2019/050184, filed Mar. 5, 2019 and published as WO 2019/169432 A1 on Sep. 12, 2019, in English, which claims priority from Australian provisional patent application 2018900739, filed Mar. 7, 2018, the contents of which are hereby incorporated by reference in their entireties.

FIELD OF THE INVENTION

The present invention relates generally to the field of computer-based image recognition. More particularly, the invention relates to methods and systems for the identification, and optionally the quantitation of, discrete objects of biological origin such as cells, cytoplasmic structures, parasites, parasite ova, and the like which are typically the subject of microscopic analysis.

BACKGROUND TO THE INVENTION

A wide variety of biological materials are analysed by light microscopy for a broad range of reasons. One such use of microscopy is for the diagnosis of medical, veterinary and botanical diseases. For example, microscopy may be used to identify a particular type of host cell amongst other host cells, such as a cancerous cell amongst a population of normal cells. Another example is the identification of an infectious microbe amongst other biological or non-biological material in a sample. Yet a further example is the identification and quantitation of a parasite ovum species in a stool sample. Apart from any diagnostic reasons, human, animal and plant materials are also analysed microscopically in the course of research activities.

Microscopy is also used in industrial settings to identify and enumerate biological material. Bacteria and yeast are used in many industrial processes with starter cultures and process samples requiring close analysis for the purposes of quality assurance and quality control.

There is often some difficulty in correctly identifying biological material in a sample. The difficulty may arise due to the presence of non-target material such as cellular fragments, tissue debris, soil, and the like. The presence of non-target material can obscure target material, or at least create uncertainty or confusion in trying to identify potential target material. While these difficulties arise where a human microscopist is involved, these problems are more significant where a computer-implemented image recognition method is used to identify target material. While image recognition has certainly advanced in accuracy in recent years, the presence of non-target material in a sample can be a confounding factor leading to inaccurate algorithmic outputs.

Accordingly, for acceptable accuracy, many image recognition methods require the target material to be purified or otherwise treated in preparation for imaging. Methods such as centrifugation and filtration may be used to substantially isolate target material, however such methods add to material and labour costs.

Where the purification procedure is performed in the field by personnel not well versed in laboratory techniques, the potential for error is high. It is entirely possible that some or all of target material is inadvertently lost during a purification procedure leading to a deceptively low count, or even a false negative result. Given the increasing use of remote diagnostic systems which negate the need to physically transport a sample to a diagnostic laboratory, sample preparation is more often in the hand of the consumer.

It is an aspect of the present invention to provide methods, systems and apparatus allowing for the reliable detection and identification of biological materials by computer-implemented image recognition means. It is a further aspect to provide an alternative to prior art methods, systems and apparatus for the detection and identification of biological materials.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

In a first aspect, but not necessarily the broadest aspect, the present invention provides a method for training a computer-implemented learning method to identify a target biological material in a sample, the method comprising the steps of accessing a plurality of training images, the training images being obtained by light microscopy of one or more samples containing a target biological material and optionally a non-target biological material, cropping one or more of the plurality of training images by human and/or computer means so as to produce one or more cropped images, each of the one or more cropped images showing predominantly the target biological material, by human means identifying the target biological material in each of the one or more cropped images where identification is possible, associating an identification label with each of the one or more cropped images where identification was possible, applying a computer-implemented feature extraction method to each labelled cropped image, applying a computer-implemented learning method to each labelled cropped image, wherein the computer-implemented learning method is configured to associate one or more extracted features of a biological material with a target biological material.

In one embodiment of the first aspect, the cropping one or more of the plurality of training images comprises distinguishing the target biological material from the microscopy field background and/or non-target material (where present), and cropping around the target biological material such that the image comprises predominantly or substantially only target biological material.

In one embodiment of the first aspect, the distinguishing the target biological material from the non-target material is implemented at least in part by computer means.

In one embodiment of the first aspect, the distinguishing the target biological material from the non-target material is by human-assisted computer means.

In one embodiment of the first aspect, the human-assisted computer means comprises dividing a training image into a series of frames, by human means identifying the presence or absence of a target biological material in each of the series of frames, applying a computer-implemented feature extraction method to each of the series of frames, and applying a computer-implemented learning method to each of the series of frames, wherein the computer-implemented learning method is configured to associate one or more extracted features with the presence or absence of a target biological material in a frame.

In one embodiment of the first aspect, the association is used to identify the presence or absence of a target biological material in a plurality of frames that were not used in the human-assisted computer means, and where the target biological material is present cropping around the target biological material such that the image comprises predominantly or substantially only target biological material.

In one embodiment of the first aspect, each of the cropped images and/or features extracted therefrom is/are stored in a database in linked associated with its respective identification label.

In one embodiment of the first aspect, the target biological material is a discrete object.

In one embodiment of the first aspect, the discrete object is a cell organelle, a cell, a unicellular organism, an anatomical part of a multicellular organism, a multicellular organism, or a reproductive structure.

In a second aspect of the invention there is provided a database comprising a plurality of cropped images produced according to the method of any embodiment of the first aspect, each cropped image in linked associated with its identification label.

In a third aspect of the invention there is provided a database comprising one, or a set of, features extracted from a training image and produced according to the method of any embodiment of the first aspect, the one or a set of features in linked association with biological material identification information.

In a fourth aspect of the invention there is provided a method of identifying a target biological material in a sample, the method comprising:

accessing a test image of a sample obtained by microscopy, applying to the test image a computer-implemented location detection method configured to identify a location of a potential target biological material in the test image, applying to the location identified a computer-implemented feature extraction method to provide one or a set of extracted features, matching the one or a set of extracted features with one or a set of features stored on a database, the database having one or a set of features in linked association with biological material identity information.

In one embodiment of the fourth aspect, the computer-implemented location detection method comprises dividing the test image into a series of regions for analysis.

In one embodiment of the fourth aspect, the regions are overlapping with each other.

In one embodiment of the fourth aspect, the computer-implemented location detection method comprises a consideration of an outline of the target biological material.

In one embodiment of the fourth aspect, a dimension of the outline is measured or estimated.

In one embodiment of the fourth aspect, the computer-implemented location detection method comprises use of a template which approximates the shape of the target biological material.

In one embodiment of the fourth aspect, the target biological material is a discrete object.

In one embodiment of the fourth aspect, the discrete object is a cell organelle, a cell, a unicellular organism, an anatomical part of a multicellular organism, a multicellular organism, or a reproductive structure.

In one embodiment of the fourth aspect, the method comprises a computer-implemented method of counting two or more discrete objects identified by the computer-implemented location detection method.

In one embodiment of the fourth aspect, the method comprises applying to the test image a cascading or a hierarchical classification method comprising a first general classification step followed by one or more specific classification steps.

In a fifth aspect, the present invention provides a system for identifying a target biological material in a sample, the system comprising:

a microscope configured to capture an image of a sample and output the image as an electronic image file, a processor-enabled device in data communication with the microscope, the processor-enabled device configured to (i) execute part or all the method of any embodiment of the fourth aspect, or (ii) transmit the electronic image file or a feature extracted from the electronic image file to a remote processor enabled device configured to execute part or all the method of any embodiment of the fourth aspect.

In one embodiment of the fifth aspect, the system comprises a remote processor enabled device configured to execute part or all the method of any embodiment of the fourth aspect, the remote processor enabled device being in data communication with the processor-enabled device in data communication with the microscope.

In one embodiment of the fifth aspect, the processor enabled device in data communication with the microscope is a mobile device.

In a sixth aspect of the present invention there is provided a processor-enabled device, or a network of processor-enabled devices configured to execute the method of any embodiment of the fourth aspect.

DETAILED DESCRIPTION OF THE INVENTION INCLUDING PREFERRED EMBODIMENTS

Figure 1:
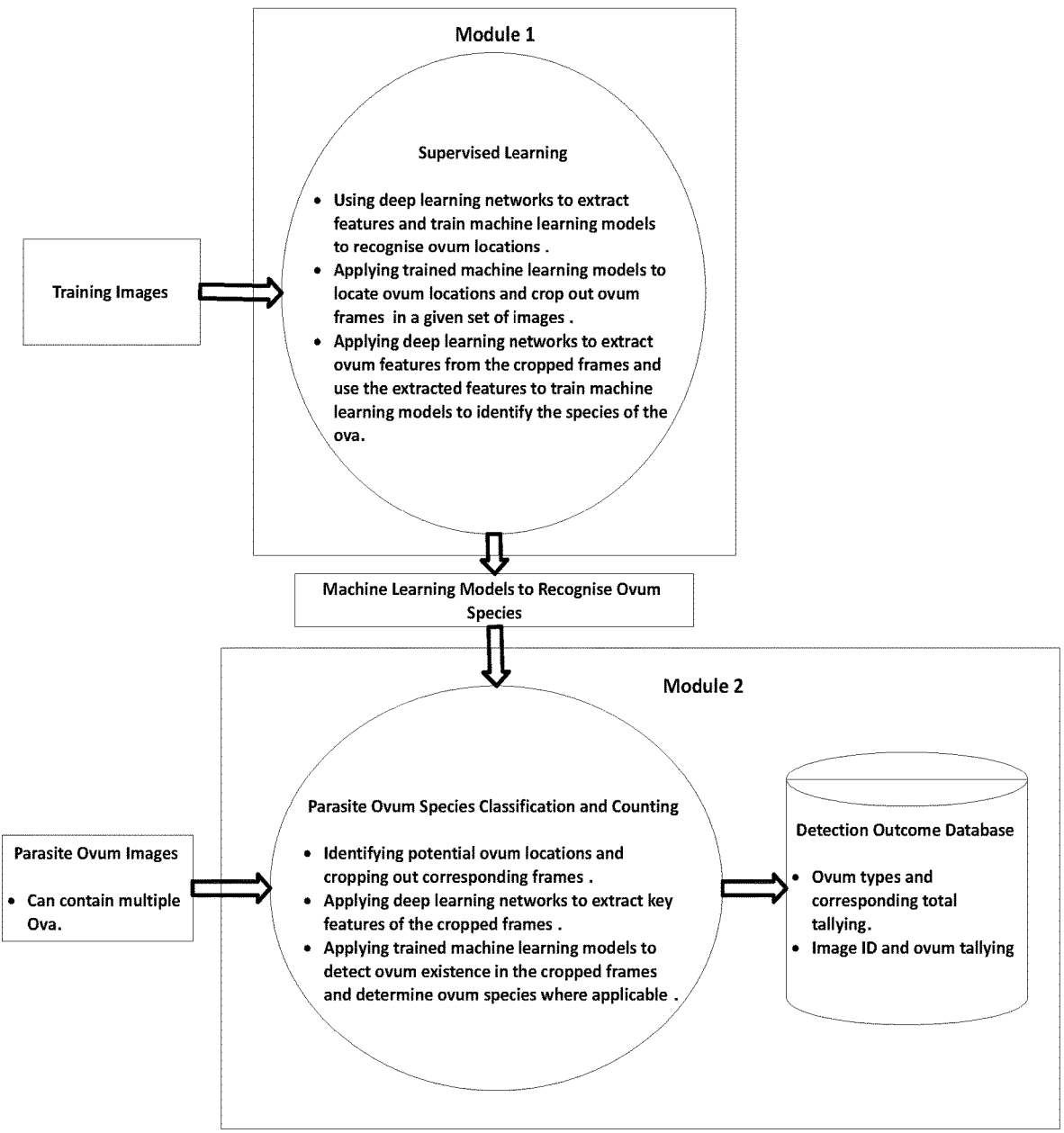
FIG. 1 is a diagrammatic representation of a preferred embodiment of the present invention used to analyse a clinical sample from an animal for parasite ova. The first module is a training module whereby a machine-learning system is taught by an expert human to identify parasite ovum locations in a microscopy image, and then crop the potential ova from the image. Once trained to identify ovum locations, a plurality of further ovum locations are automatically identified and the ova at the identified locations are cropped. The cropped images are used as input for a machine learning model for training to identify the ovum species within each cropped frame. The second module is executed on a clinical sample requiring testing for parasite infestation. This module exploits the training of the first module to first identify the location of an ovum in a microscopy field, and then where an ovum location is identified the ovum is cropped out of the image. The cropped image is then identified by reference to the ovum species training of the first module. Any identified ova may be further enumerated.

After considering this description it will be apparent to one skilled in the art how the invention is implemented in various alternative embodiments and alternative applications. However, although various embodiments of the present invention will be described herein, it is understood that these embodiments are presented by way of example only, and not limitation. As such, this description of various alternative embodiments should not be construed to limit the scope or breadth of the present invention. Furthermore, statements of advantages or other aspects apply to specific exemplary embodiments, and not necessarily to all embodiments covered by the claims.

Throughout the description and the claims of this specification the word "comprise" and variations of the word, such as "comprising" and "comprises" is not intended to exclude other additives, components, integers or steps.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may.

The present invention is predicated, in one aspect, at least in part on the finding that machine learning techniques may be used to identify the presence or absence of target biological material, and in some cases discern between variants of a general class of biological material.

Furthermore, training methods that allow for the automatic or semi-automatic detection of the location of a target biological material within a microscope field of view facilitate machine training by rapidly generating cropped images of biological material for identification and the application of a label by an expert human. Such means for locating biological material is also applied to a sample under test, and the identification algorithms (as established in the learning phase) may be applied to each cropped image from the microscope field view of a test sample.

Much of the disclosure and the studies described herein pertain to the identification of animal parasite ovum species, however it will be appreciated the same principles will be effective for other biological materials viewable by microscopy including but not limited to entire parasites (such as protozoa, helminths, and ectoparasites), host cells (including blood cells, tissue cells, and gametes), bacteria, fungi, yeasts, moulds, mycoplasma, and the like. Accordingly, where the term "ovum: or "ova" is used herein, it is to be understood that the word "structure", "cell", "organelle", "organism", "anatomical part", or "reproductive structure" may be substituted.

Applicant has applied machine learning technologies to allow for the identification of different species of parasite ova, and without the need for a human microscopist. More particularly machine-based, and particularly machine learning-based techniques are used in the present invention to extract features from microscopy images of ova in a test sample, and furthermore identify the ovum species based on supervised training with data sets. Correct identification of the ovum species is informative as to the therapy that may be offered to the host animal concerned.

In broad terms, the detection methods firstly locate parasite ova in an electronic image of a magnified field, and secondly extracts morphological features of each located ovum. It has been found that extracted features may be characteristic of a certain genus of parasite ovum, and in some cases can be used to discriminate between the ova of different species with a high level of accuracy. The present methods may further include means for counting any identified ova so as to estimate the infestation load for an animal.

In one aspect, the present invention provides a method for training a computer-implemented learning method to identify a target biological material in a sample, the method comprising the steps of accessing a plurality of training images, the training images being obtained by light microscopy of one or more samples containing a target biological material and optionally a non-target biological material, cropping one or more of the plurality of training images by human and/or computer means so as to produce one or more cropped images, each of the one or more cropped images showing predominantly the target biological material, by human means identifying the target biological material in each of the one or more cropped images where identification is possible, associating an identification label with each of the one or more cropped images where identification was possible, applying a computer-implemented feature extraction method to each labelled cropped image, applying a computer-implemented learning method to each labelled cropped image, wherein the computer-implemented learning method is configured to associate one or more extracted features of a biological material with a target biological material.

As used herein, the term "extracted feature" and variations thereof is intended to mean any feature that can be extracted from an electronic image file that may be useful in the identification of any biological material, or in the discrimination of one biological material from another, or in the discrimination of a target biological material from a non-target biological material.

Central to feature extraction is a reduction in the resources required to describe a large set of data. When performing analysis of complex data one of the major problems stems from the number of variables involved. Analysis with a large number of variables generally requires a large amount of memory and processing power, also it may cause a classification algorithm to overfit to training samples and generalize poorly to new samples.

Feature extraction is a general term for methods of constructing combinations of the variables to avoid these problems while still describing the data with sufficient accuracy.

Feature extraction typically starts from an initial set of measured data and builds derived values (features) intended to be informative and non-redundant, facilitating the subsequent learning and generalization steps, and in some cases leading to better human interpretations. Feature extraction is related to dimensionality reduction.

Thus, when the input data to an algorithm is too large to be processed and it is suspected to be redundant (e.g. the repetitiveness of images presented as pixels), then it can be transformed into a reduced set of features (a feature vector). Determining a subset of the initial features is called feature selection. The selected features are expected to contain the relevant information from the input data, so that the desired task can be performed by using this reduced representation instead of the complete initial data.

The term "crop" and variations thereof is intended to mean any substantial isolation of an image area from a surrounding image area. The acting of cropping may include the extraction of an image area to another image file, or the copying or an image area to another file. In both cases the image surrounding the image area is removed. Alternatively, the cropped image area remains with the surrounding image, however the surrounding image is disregarded in any subsequent analysis such as feature extraction.

In one embodiment, features are extracted from an image using a geometry-based approach relying on the generation of geometric models of objects. Such approaches can account for appearance variations due to viewpoint and illumination change. The geometric description of a three dimensional object allows the projected shape to be predicated in a 2D image, thereby facilitating recognition using edge or boundary information. Useful methods may rely on the extraction of geometric primitives (such as lines and circles) that are invariant to viewpoint change. An issue that may be considered by the skilled artisan is that such primitives can only be reliably extracted under limited variations in lighting, viewpoint and occlusion.

Other extraction approaches rely on appearance-based techniques which are useful in recognizing generic objects across different viewpoint and modeling illumination variation. Discriminative classifiers such as neural networks with radial basis function, dynamic link architecture, Fisher linear discriminant, support vector machines, sparse network of winnows, and boosting algorithms have been applied to recognize 3D objects from 2D images.

Thus use of feature-based algorithms is another approach whereby interest points are identified that are invariable to change due to scale, illumination and affine transformation. Such approaches can extract features that are insensitive due to scale and illumination changes, and are therefore may be utilised in the context of the present invention where variations in light and magnification of a microscope can be expected.

In one embodiment of the methods, the feature extraction comprises extracting potentially identification-relevant features from an electronic image file. In one embodiment of the method, the identification-relevant features are vectors.

In one embodiment of the method, each of the vectors is a point in a high dimensional domain. In one embodiment of the methods, the vector has at least 256, 512, 1024, 2048, or 4096 numerical values.

In one embodiment of the method, the step of extracting potentially identification-relevant features from the image file comprises use of a scale-invariant feature transform algorithm, or functional equivalent thereof, or a speeded up robust features algorithm or functional equivalent thereof.

Reference is now made to FIG. 1 showing a highly preferred scheme for (i) training a computer to crop frames containing ova in a training image ("Module 1") and (ii) classifying ova which have been cropped ("Module 2").

In this exemplary form of the invention, the training method (Module 1), is a learning process utilizing training images as input, involves the application of computer vision techniques, machine learning technologies, and human-supervised learning algorithms to crop out ova (which are confirmed as such by a supervising human) from the training images. These cropped frames are subsequently used to train a machine learning model to identify ovum species. Further details of the training method are provided infra.

In this exemplary form of the invention, the Parasite Ovum Species Classification and Counting process, and a Detection Outcome Database (Module 2) accepts as input Parasite Ovum Images and Machine Learning Models to Identify Ovum Species. Potential ova are identified from the parasite ovum images, and a deep convolutional neural network applied to extract features (and preferably identification-relevant features), and the features then used to determine the ovum species by reference to a reference database. The detection outcomes are then stored in a database where ovum species tallying may be queried.

The database may be of any type capable of performing the functions described herein. Generally, the database is of the relational type, and may be a custom coded database, or a commercially available database such as Advantage Database Server, Altibase, Apache Derby, Cubrid, Datacom, DB2, Drizzle, Empress Embedded Database, FileMaker, Firebird, HSQLDB, H2, Informix Dynamic Server, Ingres, InterBase, LucidDB, MAriaDB, MaxDB, Microsoft Access, FoxPro, Microsoft SQL Server, MonetDB/SQL, mSQL, Nexusdb, Omnis Studio, OpenLink Virtuoso, Oracle, Rdb, Paradox, Peoplesoft, Pervasive PSQL, Polyhedra DBMS, Postgre SQL, RDM embedded, RDM server, SAP, ScimoreDB, smallSQL, SQL Anywhere, SQL Base, SQLite, Unidata and Xeround Cloud Database.

Turning now to further description of the machine learning method to identify parasite ova, a significant volume of training data (i.e. a plurality of ovum images) is preferably used. Within the volume of training data used, consideration should be given to ensuring that sufficiently diverse images are used to improve the likelihood that the method is able to reliably distinguish between parasite ova of interest and other image content such as pollens and debris present in a faecal matter sample. It would be of little use to perform training using images of highly purified material given that the computer would not be taught to discriminate target material from non-target material.

The training data typically comprises image-label pairs, in which an image frame containing an ovum of known species is cropped from microscope-captured images, and labelled according to the known species as decided by a human expert. The cropping process is a preferred step as images may typically contain a variety of non-target objects present in a faecal matter sample, image noise, and other artefacts. These image-labelled pairs are then used to train an ovum classification method using machine learning training techniques.

While the cropping process may be performed manually by a human expert, higher throughput may be gained by the implementation of a semi-automatic process to obtain cropped frames by a training method and then applying machine learning models to automatically distinguish parasite ova from non-target image content (such as debris, pollen, and image noise).

Figure 2:
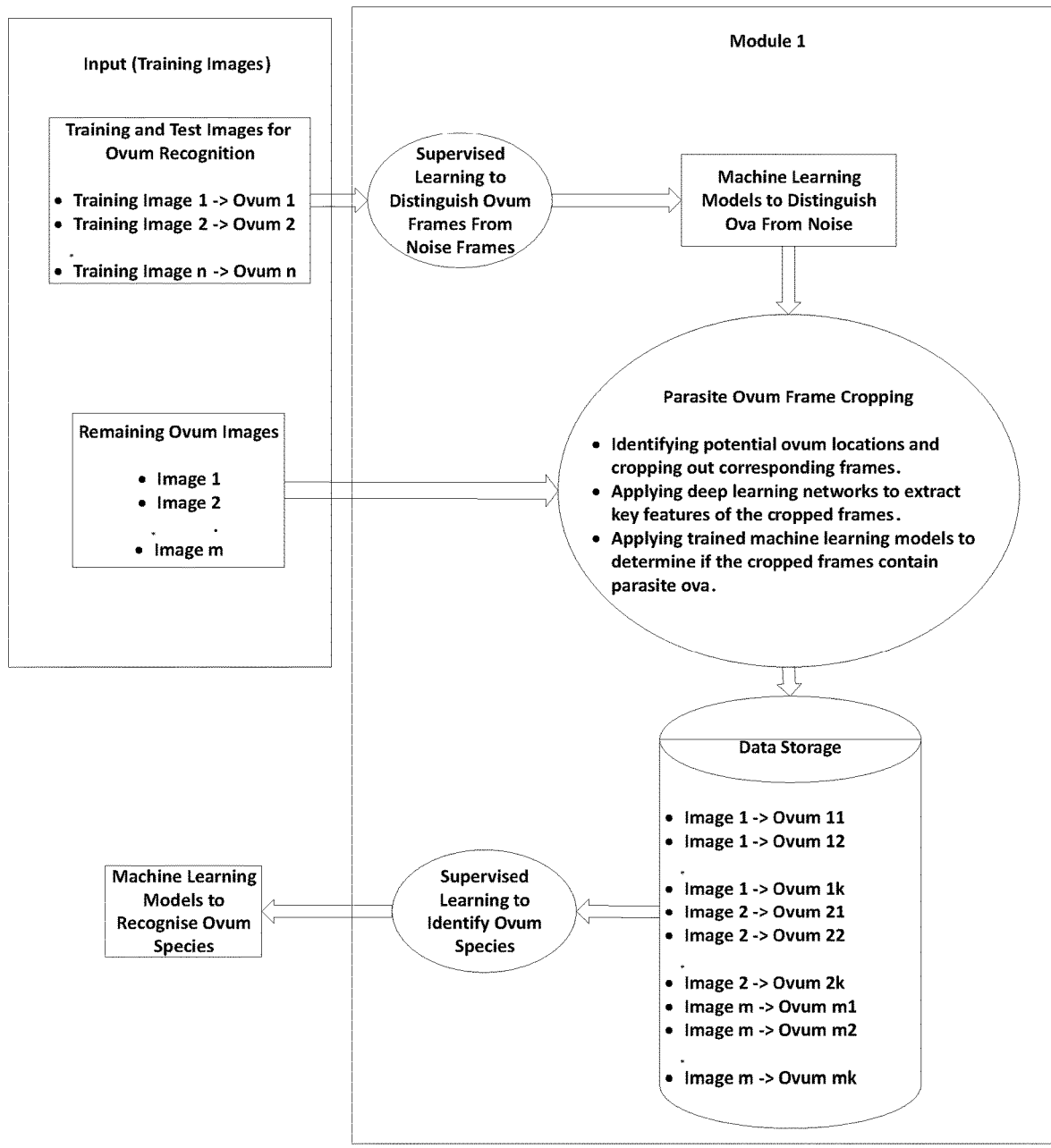
FIG. 2 is a diagrammatic representation of the data flow within the first module of FIG. 1.

An exemplary method for obtaining cropped image is shown in FIG. 2 in which a first step is defined as follows. From the set of training images parasite ova (being the input to Module 1 in FIG. 1) are identified, and a random selection of a subset of images is made (Training and Test Images for Ovum Identification) and Supervised Learning to Distinguish Ovum Frames From Noise Frames is applied. For each of the selected images, a supervising human (generally being an expert microscopist) manually identifies and crops out frames that contain parasite ova or noise. For each frame, a pre-trained, deep convolutional neural network is applied to extract morphological features. The network has been pre-trained to classify 1000 different object categories. The second-to-last layer of this network is taken, which effectively represents a set of key features for the image, from which the ovum classifier is trained. As discussed supra, training samples should provide sufficient coverage of the expected noise conditions of test images. The extracted features are used to train Machine Learning Models to Distinguish Ova From Noise.

In reference to the exemplary method for obtaining cropped image shown in FIG. 2, a second step is defined as follows. For the Remaining Ovum Images, the Parasite Ovum Frame Cropping process first identifies and crops out potential ovum frames from each of the images. Each potential ovum frame is then fed into a deep convolutional neural network to extract corresponding features. The Machine Learning Models to Distinguish Ova From Noise are then used to determine if the corresponding frame contains a parasite ovum.

In reference to the exemplary method for obtaining a cropped image shown in FIG. 2, a third step is defined as follows. The cropping outcomes are transmitted into Data Storage where information about cropped frames, such as the corresponding ovum type (such as ovum genus or species) and its original parasite image, are stored in linked association. The cropped frames in the data storage are then manually organised into groups according to their corresponding genus or species. Manual checks may also performed at this stage by an expert human supervisor to ensure the validity of the information held in the database.

In reference to the exemplary method for obtaining cropped image shown in FIG. 2, a fourth step is defined as follows. The cropped images are then used as input into the Supervised Learning to Identify Ovum Species process to train Machine Learning Models to Identify Ovum Species.

The outcome of the four step method described supra is the rapid preparation of cropped ovum frames which are used as training data for the ovum type classification.

Preferably, the first, second, third and fourth steps are carried out in that sequence.

Figure 3:
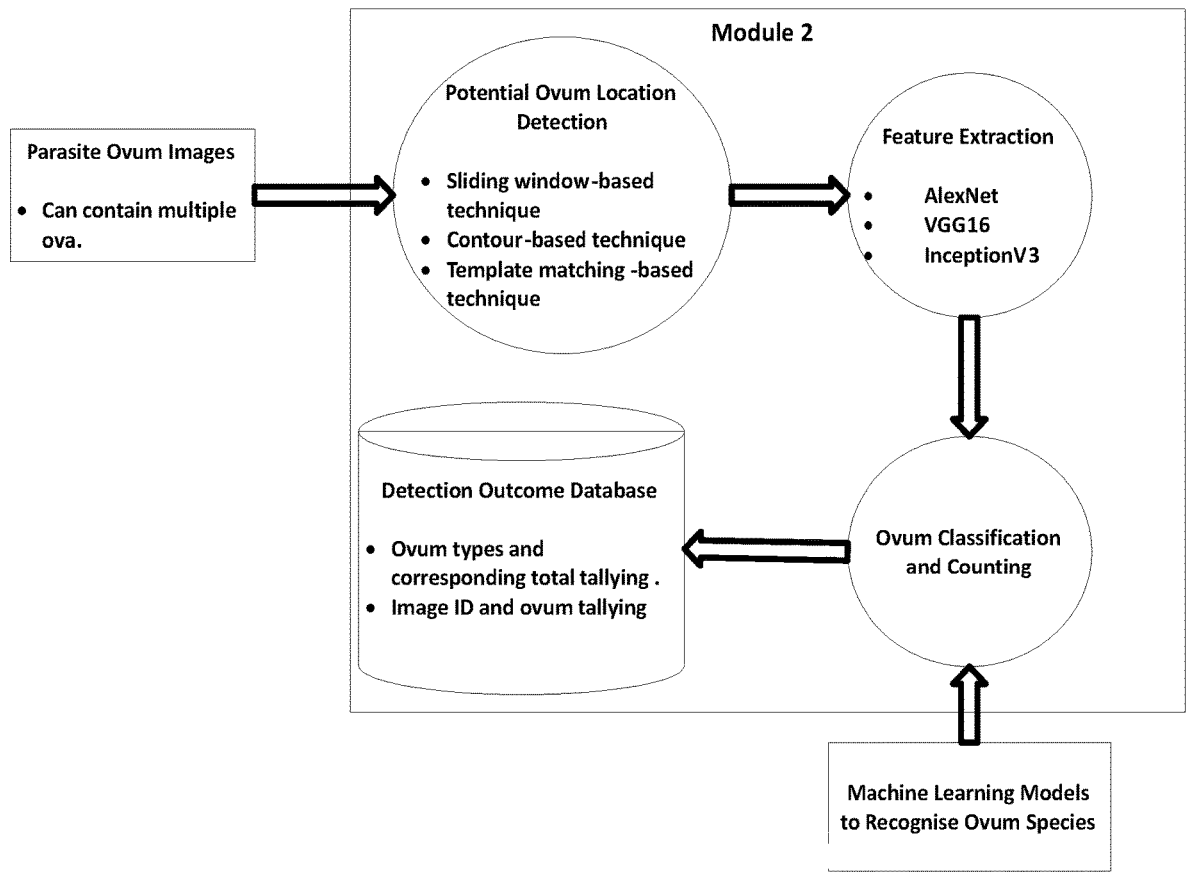
FIG. 3 is a diagrammatic representation of the data flow within the second module of FIG. 1.

Turning now to further description of the parasite ovum identification method of Module 2, reference is made to FIG. 3.

In reference to the exemplary method for parasite ovum identification shown in FIG. 3, a first step is defined as follows. Given an input image, potential ovum locations are detected using the Potential Ovum Location Detection process. The process involves the use of either sliding window-based, contour-based, or template matching-based techniques as described more fully infra.

In reference to the exemplary method for parasite ovum identification shown in FIG. 3, a second step is defined as follows. Given a potential ovum location, a corresponding frame is cropped out of the input image, and the corresponding features of the frame are extracted using the Feature Extraction process. The Feature Extraction is carried out using a neural network, more preferably a convolutional neural network, and still more preferably a deep convolutional neural network.

Convolutional neural networks are feedforward networks in so far as information flow is strictly unidirectional from inputs to output. As for artificial neural networks, convolutional neural networks are modelled on biological networks such as the visual cortex of the brain. A convolutional neural network architecture generally consists of a convolutional layer and a pooling (subsampling) layer, which are grouped into modules. Either one or more fully connected layers, as in a standard feedforward neural network, follow these modules. Modules are typically stacked to form a deep convolutional neural network. These networks consist of multiple computational layers, with an input image being processed through these layers sequentially. Each layer involves different computational operations such as convolutions, pooling, etc., which, through training with labelled images, learn to extract features relevant to classification of these objects, with the outcome at each layer being a vector containing a numeric representation of the image features. Multiple layers of feature extraction allow for increasingly complex and abstract features to be inferred (both morphological and non-morphological). The final fully connected layer outputs the class label. Despite this being a common base architecture, variations are contemplated to improve ovum classification accuracy.

The feature extraction process may be executed by way of any suitable out through the use of convolutional neural network deemed suitable by the skilled person and many of which are publicly available. Such neural networks have been pre-trained and tested on a very large dataset containing more than 1 million images across 1000 object categories (including commonly encountered objects such as animals, vehicles, food utensils, furniture etc). Exemplary deep convolution neural networks include AlexNet (8 layers, first 5 being convolutional layers followed by fully connected layers), VGG-16, and InceptionV3. The skilled artisan is familiar with such neural networks and other that will find use in the context of the present invention.

It is not necessary that all layers of a convolutional neural network are exploited. The present methods may utilise the outcome at the second-to-last layer of a convolutional neural network. This layer provides a feature vector containing 4096 numerical values, each representing a specific feature of the input image. To perform the final classification of a potential parasite ova, a Support Vector Machine may be trained to recognise the ova of interest, using this neural network provided feature vector representation of the image.

It will be understood by the skilled artisan that the specific features being extracted by the neural network are abstractions of the original image, and do not necessarily represent features easily visualised for human inspection. The abstractions are the result of many layers of convolutional processing, connecting relationships between image components across the image, and at multiple scales.

In reference to the exemplary method for parasite ovum identification shown in FIG. 3, a third step is defined as follows. The Ovum Classification and Counting process utilises the extracted features and pre-trained Machine Learning Models to Identify Ovum Species from Module 1 to identify the existence of a parasite ovum and determine the ovum type.

In reference to the exemplary method for parasite ovum identification shown in FIG. 3, a fourth step is defined as follows. The classification and counting outcomes and associated information are then stored in the Detection Outcome Database.

Preferably, the first, second, third and fourth steps are carried out in that sequence.

With reference to potential ovum location identification methods, in one exemplary form thereof potential ovum frames are identified in an image. The size of the frame may be predetermined according to an expected ovum size. The frame may be further configured such that the frame centre substantially coincides the centroid, or a central region, of an expected parasite ovum.

With regard to Module 1, a potential ovum frame is identified and thereafter cropped out of the input image and then used as input for the machine learning models to determine if the frame contains an actual parasite ova. In Module 2, potential ovum frames may be cropped out so that the species of any ovum may be identified as required according to the purpose of the application. In some applications of the present methods an identification step is unnecessary where previous analysis has identified the species and the major concern is the level of infestation. In such cases, ova may be simply enumerated. Typically, however, the method will include further steps to identify the parasite species.

In some embodiments of the method, an ovum frame is determined by a method such as a sliding window-based method, a contour-based method or a template matching-based method. The input image for each of these frame identification methods is an image that potentially contains parasite ova, and the output is (at least in circumstances where ova are in fact located) one or a set of potential ovum frames cropped out from the input image.

In reference to an exemplary sliding window-based method a first step is defined as follows. A window of fixed dimension (width and height) is used to slide through the entire input image.

In reference to an exemplary sliding window-based method a second step is defined as follows. At each position of the window on the input image, an image frame, corresponding to the current window, is cropped out.

Preferably, the first and second steps are carried out in that sequence.

To improve results, it may be necessary to optimize one or more parameters of the sliding window-based method. Window size is a first parameter that may be optimized, and may be optimized alone or in combination with any the second and/or third parameter(s). Window size may be selected according to the size of an expected parasite ovum. A frame will typically be resized before input into pre-trained deep convolutional neural networks given that the input image size used for different deep learning networks varies individually. Selection of window size may have some impact on the ovum detection outcome. As a guide, the window size will typically be sufficiently large enough so as to reasonably cover the largest expected ovum type, but should not be so large that details of the ovum appearance (especially for small ovum species) are lost when the frame is resized.

Overlapping ratio is a second parameter that may be optimized, and may be optimized alone or in combination with the first and/or third parameter(s). Where the sliding window stride length is less than the width/height of the window then adjacent windows will overlap with each other. Overlapping windows may improve location of an ovum that resides only partially within a single window, and as such the ovum features extracted from the corresponding frames will be incomplete. The overlapping ratio can be optimized, depending on the size of the parasite ovum species, to lower the likelihood that a parasite ovum is not fully residing in any window.

Merging threshold is a third parameter that may be optimized, and may be optimized alone or in combination with the first and/or second parameter(s). Where a parasite ovum (partly or fully) resides in two or more adjacent overlapping windows, a merging threshold may be implemented to avoid duplicate counting of the ovum. An ovum is only counted once even where it appears in multiple adjacent windows if the overlapping area between these adjacent windows exceeds the merging threshold. Formally, the condition may be stated as follows:

$$\text{Merging threshold} \leq \text{Overlapping area}/(\text{sum of individual area})$$

Figure 4:
FIG. 4 shows a light microscopy field of a clinical sample showing a preferred sliding window-based method for locating potential ova. A potential ovum is shown in grid area number 18. Debris is shown scattered throughout the microscopy field. In this embodiment, a window overlaps with others. For example, window number 1 (in bold outline) overlaps with window numbers 2, 6, and 7.

Reference is made to FIG. 4 which shows an exemplary sliding window-based method where the overlapping ratio is 50%; which means adjacent windows might overlap up to 50% of their individual area.

Turning now to an exemplary contour-based method for ovum location in an image field, the contour used may relate to an edge or an outline of the ovum.

In reference to an exemplary outline-based method a first step is defined as follows. For the input image, the outlines of all potential ova in the image are identified.

In reference to an exemplary outline-based method a second step is defined as follows. For each outline, its centroid is computed. Based on the centroid, a frame is constructed having a predetermined width and height. The frame has a centre which is positioned to be coincident with the centroid of the ovum.

In reference to an exemplary outline-based method a third step is defined as follows. Each of the constructed frames is considered as a potential ovum frame.

Preferably, the first, second and third steps are carried out in that sequence.

To improve results, it may be necessary to optimize one or more parameters of the outline-based method.

Outline size is a first parameter that may be optimized, and may be optimized alone or in combination with any one of more of the second, third or fourth parameter(s).

The input image may comprise digital noise artefacts, and/or contain debris such as pollens which can mimic or obscure a parasite ovum or other target biological material. Processing all outlines detected in the image may be time-consuming and so to expedite the process, a filtering step may be carried out. The filtering step selects outlines for further processing based on their size. The size thresholds (including maximum and minimum values) are determined based on the typical size of the parasite ovum species.

Predetermined frame size is a second parameter that may be optimized, and may be optimized alone or in combination with any one or more of the first, third, fourth and fifth parameter(s). Given an outline from the input image, a frame whose centre is the centroid of the outline is constructed and cropped out. The process of optimizing the frame size is similar to that for the window size in the sliding window-based method, and reference is made to that method at this point of the specification.

Merging threshold is a third parameter that may be optimized, and may be optimized alone or in combination with any one of more of the first, second, fourth and fifth parameter(s). Given an outline from the input image, a frame having a centre that is the centroid of the outline is constructed and cropped out. The process of optimizing the frame size is similar to that of optimizing the window size in the sliding window-based technique.

Histogram equalisation and image sharpening are fourth and fifth parameters that may be optimized, and may be optimized alone or in combination with any one of more of the first, second, third parameter(s). Moreover, any one or more of the first, second, third parameter(s) may be optimized independently with either the fourth parameter or the fifth parameter. Apart from the first, second, and third parameters, the fourth parameter may or may not be combined with the fifth parameter.

Depending on the hardware used, the input image may be of low contrast, blurred or otherwise compromised. Outline detection on low contrast and/or blurred images may have low accuracy which in turn affects the ovum identification and counting process. To enhance the outline detection process, a histogram equalisation and/or unsharp masking method may be used to increase the contrast and sharpen the image before applying outline detection.

Figure 5:
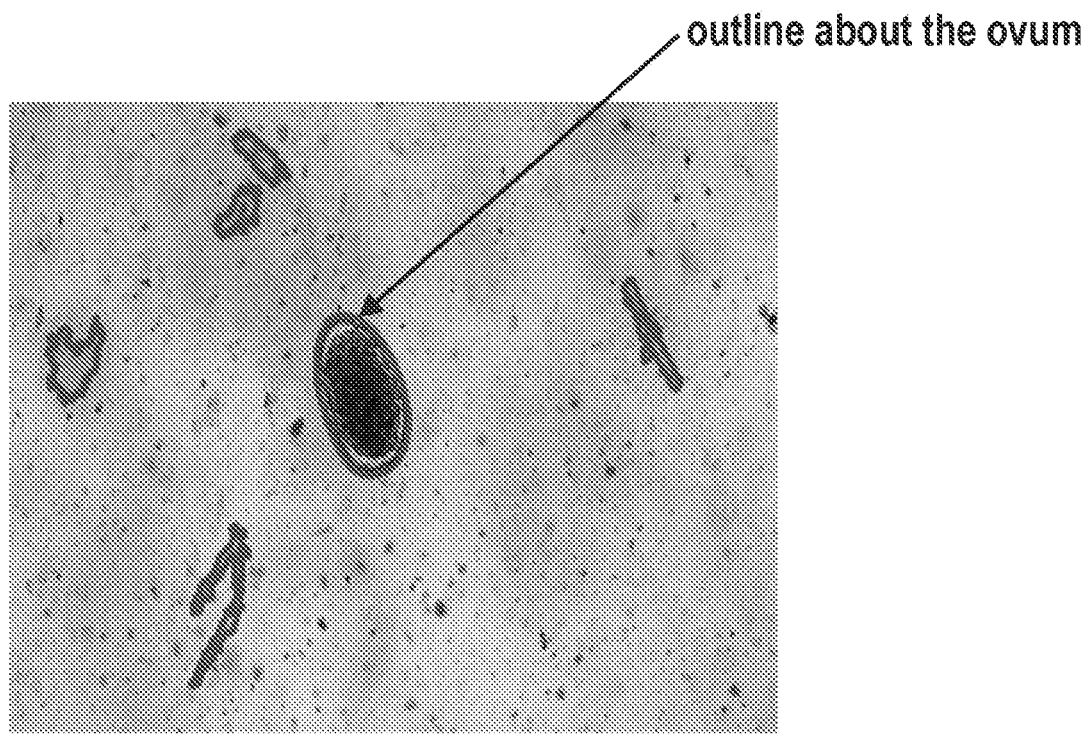
FIG. 5 shows a light microscopy field of a clinical sample showing a preferred outline-based method for locating potential ova. The method identifies the centroid and orientation of each ovum. The outline about the ovum is marked with an arrow.

Reference is made to FIG. 5 which shows an example outcome of applying outline detection on an input image. An ovoid parasite ovum is clearly shown in the centre of the figure and outlined by computer means. Items of debris are also outlined, but determined to be non-target material by the analysing computer.

In reference to an exemplary template-based method for ovum location, a first step is defined as follows. Given an input image, all contours in the image are computed.

In reference to an exemplary template-based method for ovum location, a second step is defined as follows. For each of the contours, a binary image is constructed where areas covered by the contour have a different value than the rest. A distance transform is then applied to each of the binary image. The distance transform modifies an image by changing the value at each pixel to its respective distance from the closest zero value.

In reference to an exemplary template-based method for ovum location, a third step is defined as follows. A template is constructed where the distance transform is also applied.

In reference to an exemplary template-based method for ovum location, a fourth step is defined as follows. For each of the transformed images, the template is slid through as per the sliding window-based technique. At each position of the template on the image, a matching metric is calculated corresponding to the matching level. The matching level at each position is calculated as:

$$R(x, y) = \frac{\sum_{x',y'} (T'(x', y') \cdot I'(x+x', y+y'))}{\sqrt{\sum_{x',y'} T'(x', y')^2 \cdot \sum_{x',y'} I'(x+x', y+y')^2}}$$

Where:

$$T'(x',y')=T(x',y')-1/(w \cdot h) \cdot \Sigma_{x'',y''} T(x'',y'')$$

$$I'(x+x',y+y')=I(x+x',y+y')-1/(w \cdot h) \cdot \Sigma_{x'',y''} I(x+x'',y+y'')$$

And:
T is the template image
w, h are the width and height of the template respectively.
I is the input image
R(x, y) is the matching level at coordinate (x, y) of the input image I
x, y denote x- and y-coordinates for a position in the input image I
x', y' denote x- and y-coordinates for a position in the template T
x", y" denote x- and y-coordinates for a position the template T In reference to an exemplary template-based method for ovum location, a fifth step is defined as follows. A thresholding mechanism is employed to find the outline of the matching shape. The outline was used to determine the location of the potential parasite ovum location, its orientation and estimated length/width.

In reference to an exemplary template-based method for ovum location, a sixth step is defined as follows. For each of the identified outlines, a potential ovum frame is cropped out for further processing.

To improve results, it may necessary to optimize one or more parameters of the template-based method.

Template shape and/or size is/are first parameter(s) that may be optimized, and may be optimized alone or in combination with the second and/or third parameter(s). Parasite ova may vary significantly in size and shape, choosing the shape and size of the template can impact identification accuracy. Preferably, the shape is similar to that of the target parasite ovum species. However, as ovum shapes vary, including ellipse-like shape, rectangle-like shape, shell-like shape, etc., a generally circular shape was employed to approximate the majority of objects instead of focusing on any particular shape. Template size, is typically chosen to approximate the ovum size.

Outline size is a second parameter that may be optimized, and may be optimized alone or in combination with the first and/or third parameter(s). Processing all outlines detected in the image may be time-consuming; to speed up the process, a filtering step, based on the outline size, can be carried preferably as for the contour (outline)-based method described supra.

Potential ovum area is a third parameter that may be optimized, and may be optimized alone or in combination with the first and/or second parameter(s). Once the location of an ovum is known, and its length/width estimated, the area containing the ovum is cropped for further analysis. The cropped area is estimated by investigating the typical size of the ovum species, and may therefore be pre-specified according to certain threshold.

Figure 6A:
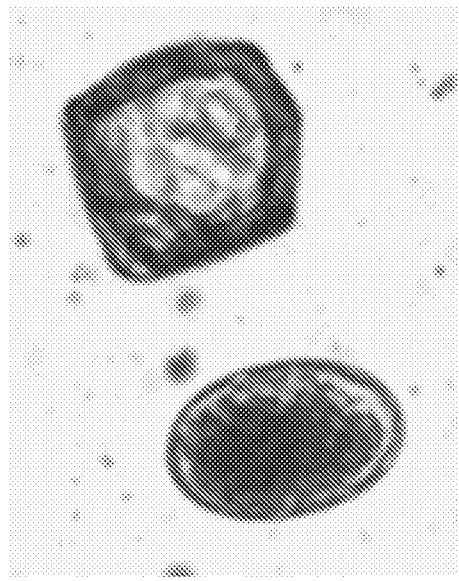
FIG. 6A shows a light microscopy field of a clinical sample, and FIG. 6B templates of a preferred template-based method for locating potential ova. The technique successfully identifies the centroid and orientation of each ovum.
Figure 6B:
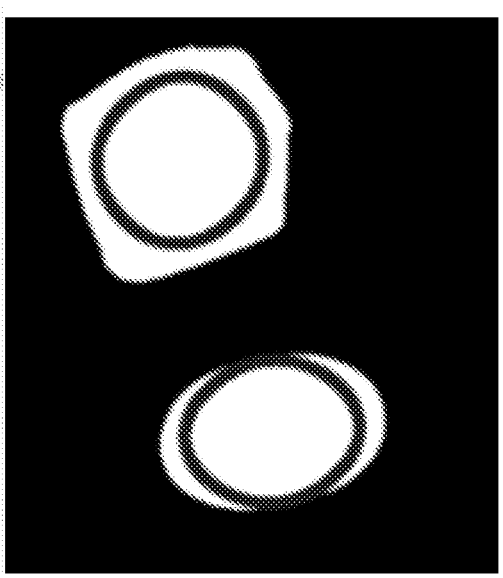

Reference is made to FIG. 6 which shows the result of applying a template matching-based method to a clinical sample input image.

The decision as to whether to use sliding window-based, contour-based, or template matching-based techniques may be taken having consideration the nature of the input images: The contour-based methods are generally the fastest, however may be sensitive to noise. When the level of noise is high, a sliding window-based method is generally preferred over a contour-based method.

Both the sliding window-based and contour-based methods are generally less preferred where the input images comprise clusters of ova, and particularly in circumstances where the ova touch or connect to each other in some manner. In these cases, template matching-based methods are generally more useful.

The ovum identification process may be further optimized as follows. As input images may contain digital noise, and furthermore different ovum species can be very similar in appearance to each other under light microscopy, applying only a single classifier may not be sufficient to achieve acceptable accuracy in identifying ovum species against noise. To improve classification accuracy, cascading multiple classifiers may be used.

In the context of the present invention, a cascading process may be defined as a process including two or more classification methods and further including at least one decision point to select which of the two or more methods to use depending on the outcomes of a previous step. This dynamic approach to optimisation is based on an analysis of classification error for each species.

Figure 7:
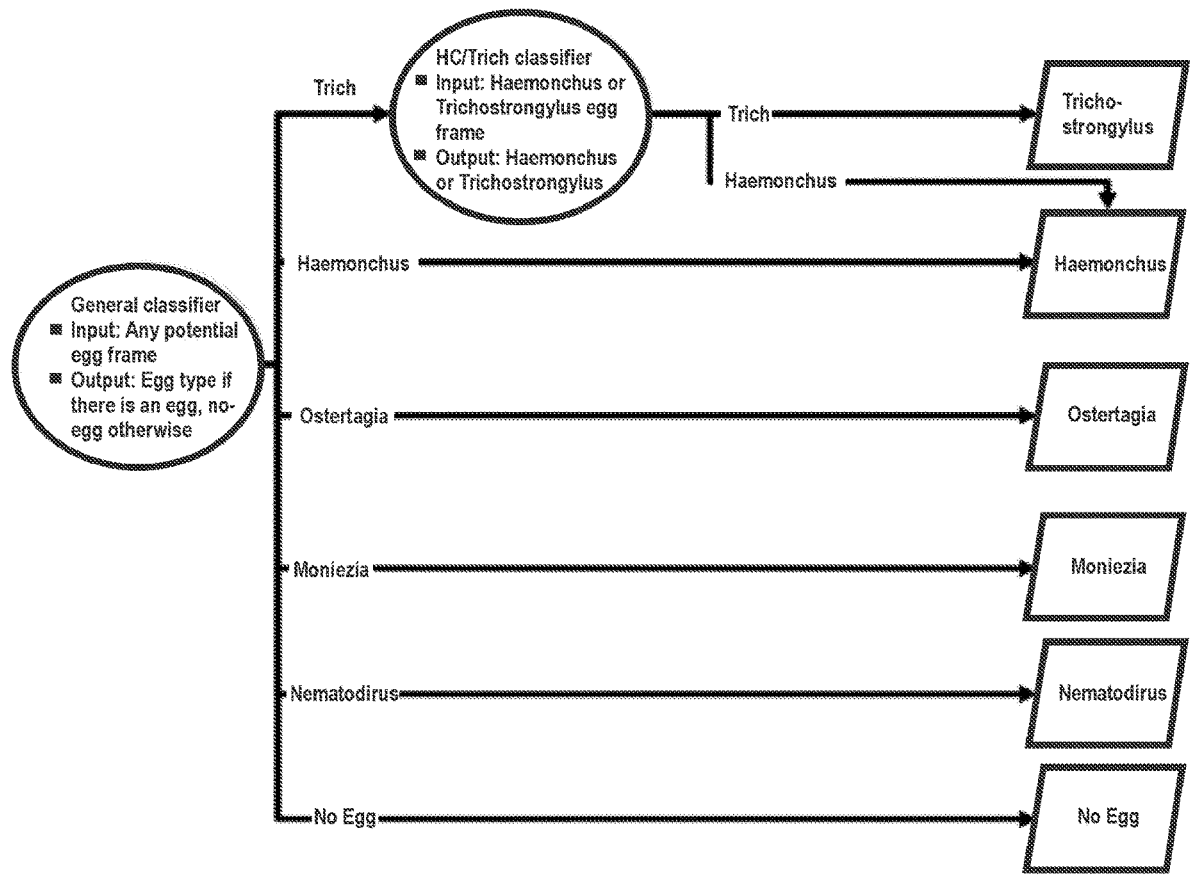
FIG. 7 is a diagrammatic representation of a preferred parasite ovum classification process after analysing false negative rates for *Haemonchus* ova using only a general classifier. In the figure, HC stands for *Haemonchus*, Trich stands for *Trichostrongylus*.
Figure 8:
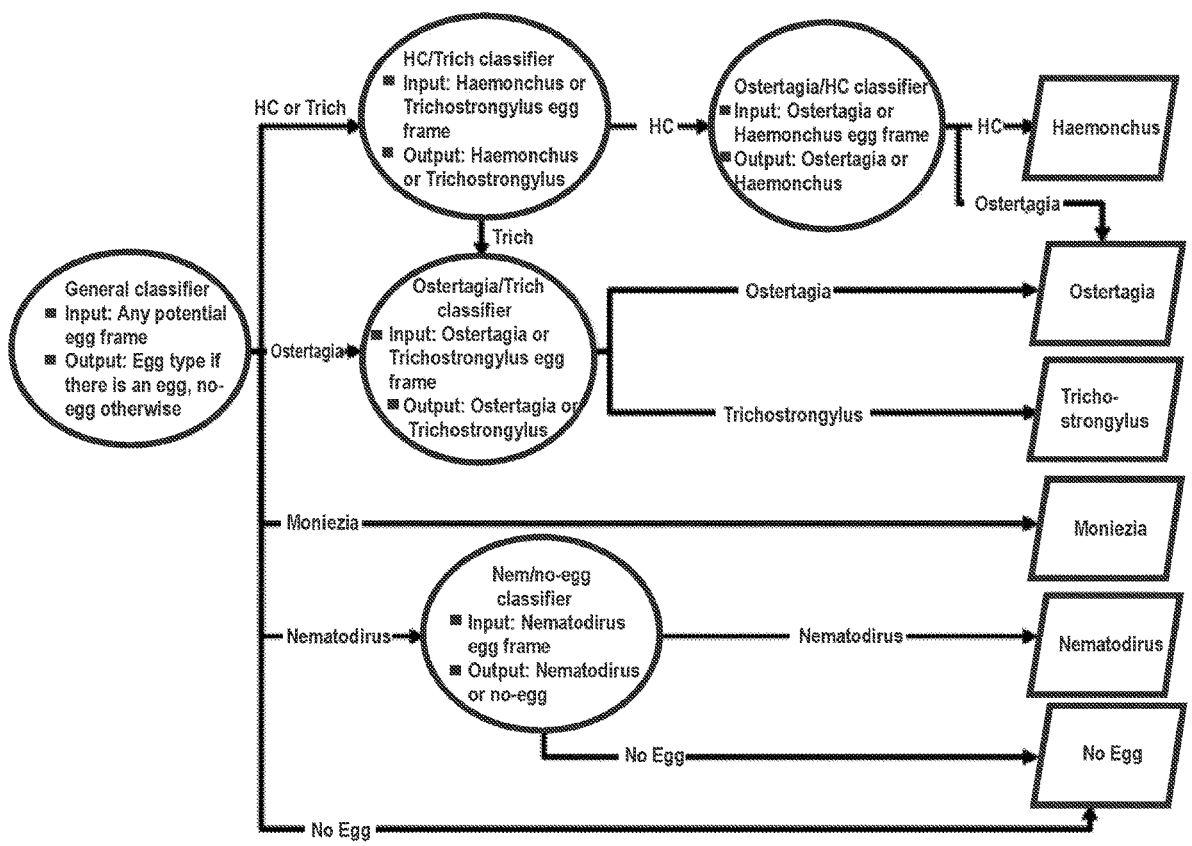
FIG. 8 is a diagrammatic representation of preferred complete parasite ovum classification process. In the figure, HC stands for *Haemonchus*, Trich stands for *Trichostrongylus*, Nem stands for Nematodirus.

Reference is made to FIG. 7 and FIG. 8. The cascading process (which may also be considered a hierarchical process) starts by applying a general classifier to a set of current input images. The general classifier is a classifier configured, at least to some extent, to potentially distinguish all expected species, including non-ovum objects. The generally classifier may misidentify some ovum species, and may therefore output a false negative result for a given species.

The classification errors for each parasite ovum species from the general classifier guide the decision as to which step should be executed next in the classification system of the process. For each of the species, the rates at which that species is misidentified is analysed. These rates are considered to be false negative rates of an ovum species with respect to others. The false negative rate of a parasite ovum type with respect to another (as shown in Eq. 1) is defined as the fraction of the number of cases where the former is misidentified as the latter out of the total number of the former's false negative cases.

$$\text{False\_Negative\_Rate}_{A\ w.r.t.\ B} = \frac{\sum \text{Misrecognition}_{A\ as\ B}}{\sum \text{False\_Negative}_A} \quad (1)$$

In the above formula, the term "misrecognition" is taken as the equivalent of "misidentification".

In the following, a series of method steps are defined in reference to the classification of five exemplary parasite ovum species of the genera: *Haemonchus*, *Moniezia*, *Nematodirus*, *Ostertagia*, and *Trichostrongylus*.

As a first step, the general classifier is applied. The general classifier is used as the starting point as at this stage, there is no information available relating to false negative rates for any ovum genus.

As a second step for each of the parasite ovum species identified by the general classifier, its false negative rates are calculated with respect to other genera. For example, a sample of outcomes for identifying *Haemonchus* ova after applying the general classifier is shown in Table 1 below.

| True Parasite ovum Genus | Identified ovum Genus | Classification Count | False Negative Rate |
|---|---|---|---|
| *Haemonchus* (65 ova) | *Trichostrongylus* | 13 | 20% |
| | *Moniezia* | 0 | 0% |
| | *Nematodirus* | 0 | 0% |
| | *Ostertagia* | 0 | 0% |
| | Noise | 0 | 0% |
| | *Haemonchus* | 52 | N/A |

Table 1 shows false negative rates for *Haemonchus* ova with respect to other ovum types. The total number of true *Haemonchus* ova is 65; of these 65 ova, 13 ova are misidentified as *Trichostrongylus*, corresponding to 20% false negative rate.

The above table shows that 20% of *Haemonchus* ova are misidentified as *Trichostrongylus*.

As a second step, for each of the parasite ovum species, select the ovum species with respect to which it has the highest false negative rate. If the highest false negative rate is smaller than an acceptable threshold, skip the current ovum genus. Otherwise, the following routine is followed:

(i) Train a new classifier to distinguish the current ovum type from the type with the highest false negative rate, and (ii) Create a branch connecting any classifier, which (1) has the highest-false-negative-rate type as one of its outputs and (2) does not have any branch associating the output of the highest-false-negative-rate type to any classifier, to the newly trained classifier.

For example, as shown in Table 1, *Haemonchus* ova have the highest false negative rate with respect to *Trichostrongylus* ova. Assuming that the acceptable threshold is 10%, using the present method, a *Haemonchus* versus *Trichostrongylus* classifer (HC/Trich classifier) needs to be trained. Once the classifier has been trained, it will be connected to the general classifier as the general classifier (1) has *Trichostrongylus* type as one of its outputs and (2) does not have any branch associating the output of *Trichostrongylus* type to any other classifier. A graphical outline of the method is shown in FIG. 7.

As a third method step, feed all input images to the current system, starting from the general classifier again, to obtain a new set of classification outcomes.

The second and third methods steps are repeated until all ovum species have their false negative rates below the acceptable threshold or there is no further significant improvement achieved.

With regard to the identification of a target biological material by reference to a database, it will be understood that the reference database will contain a label (such as a known ovum genus) for a certain biological material (an ovum) in linked association with a comparator that can be matched against a test biological material (such as a test ovum of unknown genus). The comparator may be a set of image features extracted from the known ovum and the test ovum. An alternative to that approach is the storage of a library of labelled cropped image of known ova, with an image of a test ovum being compared against each image in the library in order to identify the closest match.

A feature-based method may be used in attempting to match a test object to a reference image. In searching for feasible matches, an interpretation tree may be utilized. In such embodiments, the root node represents an empty set, and each other node is the union of the matches in the parent node and one additional match. A "wildcard" may be used for features with no match. Nodes are cut when the set of matches is infeasible.

Alternatively, a "hypothesize and test" method is used in the comparison of an object against the reference images. Such methods rely on the general approach of hypothesizing a correspondence between a collection of reference image features and a collection of object features, and then use this to generate a hypothesis about the projection from the object coordinate frame to the library image frame. This projection hypothesis is used to generate a rendering of the object (termed "back-projection"). Then follows the step of comparing the rendering to the object, and if the two are sufficiently similar, accept the hypothesis A pose consistency method may be used in the comparison of an object to reference images. This method is also based on the formation of alignments since the object is aligned to the reference image. A small number of correspondences yield the object position, and the other correspondences must be consistent. The principle is that a match is hypothesized between a large group of image features and a large group of object features, then the missing parameters can be recovered and so render the rest of the object. Hypotheses are generated using small number of correspondences. Other model features are back-projected into the image and additional correspondences verified. In this method, the smallest number of correspondences necessary to achieve discrete object poses are used.

In one embodiment of the system or method, a pose clustering method is used in the comparison of the object and reference images. The principle of this method is that each object leads to many correct sets of correspondences, each of which has (approximately) the same pose. A vote on pose is performed using an accumulator array that represents pose space for each object. For each object, an accumulator array that represents pose space is set up—each element in the accumulator array corresponds to a "bucket" in pose space. Each image in the frame group is then taken, and a hypothesis formed relating to correspondence between it and every frame group on every object. For each of these correspondences, pose parameters are determined and an entry made in the accumulator array for the current object at the pose value. Where there are large numbers of votes in any object's accumulator array, this can be interpreted as evidence for the presence of that object at that pose. The evidence may be checked using a verification method.

An invariance method may be used in the comparison of an object against reference images. This method relies on the presence of geometric properties that are invariant to camera transformations, and is therefore applicable only to certain circumstances.

A geometric hashing method may be used. This method utilizes an algorithm reliant on geometric invariants to vote for object hypotheses. It is similar to pose clustering methods, except that rather than voting on pose, there is voting on geometry.

A scale-invariant features transform (SIFT) method may be used in the comparison of the test object and reference images. By this method, keypoints of objects are first extracted from reference images and stored in the database. An object and image are individually compared feature-by-feature and finding candidate matching features based on Euclidean distance of their feature vectors.

SIFT keypoints of objects are extracted from the reference images of the database and stored in the database. From the full set of matches, subsets of keypoints that agree on the object and its location, scale, and orientation in the new image are identified to filter out good matches. The determination of consistent clusters is performed rapidly by using an efficient hash table implementation of the generalized Hough transform. Each cluster of 3 or more features that agree on an object and its pose is then subject to further detailed model verification and subsequently outliers are discarded. Finally the probability that a particular set of features indicates the presence of an object is computed, given the accuracy of fit and number of probable false matches. Object matches that pass all these tests can be identified as correct with high confidence. Further detail of the incorporation of SIFT methods into the present methods and systems are found herein with reference to the preferred embodiments.

For any feature-based method (including SIFT) putative comparison-relevant features (such as vectors) are extracted from the test image file, and also the reference image file. The vectors may be a point in a high dimensional domain.

In one embodiment of the system or method, a Speed Up robust Features (SURF) method is used in the comparison of test images and reference images. This method uses an integer approximation to the determinant of Hessian blob detector, which can be computed rapidly with an integral image (3 integer operations). For features, it uses the sum of the Haar wavelet response around the point of interest. Again, these can be computed with the aid of the integral image.

In one embodiment, the number of vector elements is configurable and is set to a minimum number, and preferably at least about 2, 4, 8, 16, 32, 64, 128, 256, 512, 1024, 2048 or 4096. The range of values for a vector are typically normalized between −1 and 1.

It will be appreciated that more than one comparison method may be used to improve accuracy. For example, a SIFT and SURF method may be used in combination.

Any of the methods disclosed herein may be performed by application software executable on any past, present or future operating system of a processor-enabled device such as Android™ iOS™, Windows™, Linux™ and the like. It will be appreciated that any software may be distributed across a number of devices or in a "software as a service" format, or "platform as a service" format whereby participants require only some computer-based means of engaging with the software. Mobile devices with associated operating system are preferred given the ability to obtain a test image in the field (for example, with a smartphone or a tablet). Such devices are easily handled, connectable to the Internet, and battery powered.

The micrograph used as the input image may be obtained from the mobile device per se, for example by the attachment of a magnifying lens and other hardware to an embedded camera of a smart phone. Such arrangements may use standard, inexpensive microscope eyepieces and objectives; with magnification and resolution able to be adjusted by changing the objectives. For example, a 0.85 NA 60× Achromat™ objective and a 20× wide field microscope eyepiece may be implements, to provide a field of view of around 180 μm diameter, an effective magnification onto the camera face of about 28×, and a spatial resolution of about 1.2 μm. Resolution of about 1.2 μm may be provided by this arrangement, based on the full width at half maximum of the system point-spread function.

As an alternative, a separate microscope is provided that is capable of the requisite magnification (for example at least about 2×, 5×, 10×, 20×, 30×, 40×, 50×, 100×, or 200×), and also of electronic capture of the magnified image. An image capture component such as a CMOS sensor may be used, the output of which is stored in an image format (such as JPG, GIF or TIFF) and stored on board in a RAM module. A regular inexpensive optical microscope may be modified to substitute the eyepiece with a digital eyepiece. The digital eyepiece captures the image as it would be seen by the human eye and outputs to a processor-enabled device (such as a smart phone or tablet) via wired or wireless protocol. In this way, a user is able to adjust lighting conditions (such as light source and diaphragm) and focus the objective so as to provide a sharp image of the sample. Once an acceptable image is gained, the digital eyepiece may be substituted in the light path so as to provide a digital image for analysis.

Use of a digitally capable microscope facilitates the use of techniques such a bright field, dark field, phase contrast, and oil immersion microscopy.

It has been surprisingly found that a microscope having even basic optics is able to provide images of sufficient quality for machine learning and identification.

More advanced microscopes and sophisticated microscopy are contemplated to be useful in the context of the present invention. For example, 3D microscopy is possibility in the context of the present invention given the ability of a microscope to scan through the depth of a transilluminated sample and for a 3D representation of the magnified structure to be constructed by software means. As another example fluorescence microscopy requires the use of tagged probes (such as antibodies) and a light source (such as UV) capable of exciting the fluorescent tag.

The digital image of the specimen may be communicated to the mobile device by wired means (such as USB or Lightning™ cable), or wireless means (such as Bluetooth™ or Ant™). The device may subsequently transmit the image to a cloud server via a cell phone system (such as 4G).

In many applications, the test image will be taken in the field, and then communicated via the Internet to a cloud server which performs any necessary feature extraction. The cloud server may also contain a library of reference labelled images or a library of labelled extracted features, and furthermore be configured to perform any feature/feature comparisons or image/image comparisons required.

An exemplary application of the present invention is where the image is taken at a remote location (i.e. away from any established means of sample analysis such as a microbiological diagnostic laboratory) where in the normal course of events there would be some difficulty and delay experienced in obtaining a diagnostic result. For example, a farmer having an animal having a suspected parasite infestation may take a stool sample, use an digitally-enabled microscope to capture a magnified image of the stool sample, and then use a smart phone to upload the image to a cloud server configured to analyse the image and identify the genus and optionally the species of any parasite ova in the sample. After the required machine analysis (which may take only several seconds or less) a parasite species identification is transmitted from the cloud server to the farmer's smart phone. The cloud server may be further configured (by algorithmic means) to identify a therapeutic agent and dosage regime capable of killing or inhibiting the detected parasite thereby allowing the farmer to immediately commence treatment of the animal.

Such diagnosis, being computer-implemented, does not require human intervention and therefore may be provided at any time or night or day, or during holiday periods when qualified diagnosticians are unavailable. Moreover, it will be appreciated that professional services fees of a diagnostic laboratory may be avoided.

As emphasised elsewhere the training and identification methods disclosed herein will be useful in many contexts. As a further example, blood cells may be differentiated from each other and enumerated so as to rapidly provide valuable information. Different red blood cells types (including size variations: normal, microcyte, macrocyte, oval macrocyte, hyochromic macrocyte; varying distributions of haemoglobin: hyochromia, polychromasia; shape variation: target cell, spherocyte, ovalcyte, stomoatocyte, sickle cell, burr cell; cells showing inclusions: Pappenheimer bodies, Cabot's ring, stippling, Howell-Jolly; agglutinated structures; and rouleaux structures) may be differentiated from each other. White bloods may also be differentiated: neutrophil, eosinophil, basophil, large lymphocyte, small lymphocyte, and monocyte.

As another potential application the present training and identification methods may be used to automate semen analysis including enumerating sperm and assessing sperm morphology including head, neck and tail defects.

Sample preparation is preferably simplified so far as possible given that such tasks will be performed in the field, and often by personnel that are not trained in laboratory methods. A sample may, for example, be simply prepared by adding a liquid diluent and after mixing being placed onto a glass slide in a "wet mount" approach.

A faecal sample may be smeared across a glass slide and allowed to dry before adding a simple ovum staining protocol such as carbol fuschin/malachite green.

While various stains and lighting conditions may be used to emphasise structures within or about a cell or a tissue. It will generally be the case that training images and test images will be prepared and illuminated under substantially the same conditions.

Extracellular bodies found in biological fluids such as urine and blood may also be identified by the present methods. Various crystals, bodies and sediments may be found in biological liquids, with many being discrete in nature and having distinctive sizes and morphologies that may be learned by a machine-learning system and then applied to a test sample.

A structure or a biomolecule of a biological material may be highlighted, and therefore more apparent on a captured image, by way of a specific staining or tagging technique. For example, a stain which binds preferentially to protein to may be used. Alternatively, a more specific tag may be used to bind to a particular nucleic acid, protein or glycoprotein motif. The tag may comprise a reporter such as a fluorescent molecule which will be detectable to an image capture means.

The present identification algorithms may be augmented to receive ancillary information which may assist to the identification process. For example, where the algorithm is configured to identify a pathogen, the algorithm may accept information such as patient history, any existing condition or other infections, geographical location, age, ethnicity, species, breed or any other information which may be used to increase the precision of identification. Such information may be used by the algorithm where an equivocal identification may otherwise result.

Improved precision may result where, for example, the algorithm has identified two potential pathogens however the geographical location of the patient makes it much more likely that the pathogen is one in preference to the other. Any co-infection may also provide further information, such as *Moniezia* ova often co-distributes with Nematodirus.

Sections of whole tissues may also be analysed according to the present methods, with cell types within the section being identifiable after a learning process. In this application, the cells will typically be in close contact with each other, and accordingly cropping around each cell will be generally more precise than situations where well separated discrete objects are involved.

As will be appreciated by the skilled artisan, the computer-implemented training and identification methods and systems described herein may be deployed in part or in whole through one or more processors that execute computer software, program codes, and/or instructions on a processor. The processor may be part of a server, client, network infrastructure, mobile computing platform, stationary computing platform, or other computing platform. A processor may be any kind of computational or processing device capable of executing program instructions, codes, binary instructions and the like. The processor may be or may include a signal processor, digital processor, embedded processor, microprocessor or any variant such as a coprocessor (math co-processor, graphic co-processor, communication co-processor and the like) and the like that may directly or indirectly facilitate execution of program code or program instructions stored thereon. In addition, the processor may enable execution of multiple programs, threads, and codes.

The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere.

Any processor or a mobile communication device or server may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In some embodiments, the processor may be a dual core processor, quad core processors, other chip-level multiprocessor and the like that combine two or more independent cores (called a die).

The methods and systems described herein may be deployed in part or in whole through one or more hardware components that execute software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, computers, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, computers, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, calculations, algorithms, and instructions described herein may be implemented on a cellular network having multiple cells. The cellular network may either be frequency division multiple access (FDMA)

network or code division multiple access (CDMA) network. The cellular network may include mobile devices, cell sites, base stations, repeaters, antennas, towers, and the like. The cell network may be a GSM, GPRS, 3G, 4G, EVDO, mesh, or other networks types.

The methods, programs codes, calculations, algorithms and instructions described herein may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon.

Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on computer readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks.

Removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on computers through computer executable media having a processor capable of executing program instructions stored thereon as a monolithic software structure, as standalone software modules, or as modules that employ external routines, code, services, and so forth, or any combination of these, and all such implementations may be within the scope of the present disclosure.

Furthermore, the elements depicted in any flow chart or block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a computer readable medium.

The Application software may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

The invention may be embodied in program instruction set executable on one or more computers. Such instructions sets may include any one or more of the following instruction types:

Data handling and memory operations, which may include an instruction to set a register to a fixed constant value, or copy data from a memory location to a register, or vice-versa (a machine instruction is often called move, however the term is misleading), to store the contents of a register, result of a computation, or to retrieve stored data to perform a computation on it later, or to read and write data from hardware devices.

Arithmetic and logic operations, which may include an instruction to add, subtract, multiply, or divide the values of two registers, placing the result in a register, possibly setting one or more condition codes in a status register, to perform bitwise operations, e.g., taking the conjunction and disjunction of corresponding bits in a pair of registers, taking the negation of each bit in a register, or to compare two values in registers (for example, to see if one is less, or if they are equal).

Control flow operations, which may include an instruction to branch to another location in the program and execute instructions there, conditionally branch to another location if a certain condition holds, indirectly branch to another location, or call another block of code, while saving the location of the next instruction as a point to return to.

Coprocessor instructions, which may include an instruction to load/store data to and from a coprocessor, or exchanging with CPU registers, or perform coprocessor operations.

A processor of a computer of the present system may include "complex" instructions in their instruction set. A single "complex" instruction does something that may take many instructions on other computers. Such instructions are typified by instructions that take multiple steps, control multiple functional units, or otherwise appear on a larger scale than the bulk of simple instructions implemented by the given processor. Some examples of "complex" instructions include: saving many registers on the stack at once, moving large blocks of memory, complicated integer and floating-point arithmetic (sine, cosine, square root, etc.), SIMD instructions, a single instruction performing an operation on many values in parallel, performing an atomic test-and-set instruction or other read-modify-write atomic instruction, and instructions that perform ALU operations with an operand from memory rather than a register.

An instruction may be defined according to its parts. According to more traditional architectures, an instruction includes an opcode that specifies the operation to perform, such as add contents of memory to register—and zero or more operand specifiers, which may specify registers, memory locations, or literal data. The operand specifiers may have addressing modes determining their meaning or may be in fixed fields. In very long instruction word (VLIW) architectures, which include many microcode architectures, multiple simultaneous opcodes and operands are specified in a single instruction.

Some types of instruction sets do not have an opcode field (such as Transport Triggered Architectures (TTA) or the Forth virtual machine), only operand(s). Other unusual "0-operand" instruction sets lack any operand specifier fields, such as some stack machines including NOSC.

Conditional instructions often have a predicate field—several bits that encode the specific condition to cause the operation to be performed rather than not performed. For example, a conditional branch instruction will be executed, and the branch taken, if the condition is true, so that execution proceeds to a different part of the program, and not executed, and the branch not taken, if the condition is false, so that execution continues sequentially. Some instruction sets also have conditional moves, so that the move will be executed, and the data stored in the target location, if the condition is true, and not executed, and the target location not modified, if the condition is false. Similarly, IBM z/Architecture has a conditional store. A few instruction sets include a predicate field in every instruction; this is called branch predication.

The instructions constituting a program are rarely specified using their internal, numeric form (machine code); they may be specified using an assembly language or, more typically, may be generated from programming languages by compilers.

Example 1: Machine Identification of Parasite Ova

A computer comprising a parasite ovum identification algorithm according to the present invention was used to identify parasite ova. A total of 65 images for each of *Haemonchus, Moniezia, Nematodirus, Ostertagia*, and *Trichostrongylus* were analysed by the computer. Results for precision and recall are shown in Table 2, below:

| Egg type | Precision | Recall |
|---|---|---|
| *Haemonchus* | 98.5% | 98.5% |
| *Moniezia* | 100% | 100% |
| *Nematodirus* | 100% | 100% |
| *Ostertagia*\* | 81.3% | 80% |
| *Trichostrongylus*\* | 80.6% | 83.1% |
| Average: | 92.08% | 92.32% |

It is contemplated that performance of the algorithm may be improved by training with a larger number of training images and/or a more diverse range of training images.

Example 2: Comparison of Crop Fit and Template-Based Methods in the Identification Process Performance of a detection algorithm using crop fit versus template-based methods was assessed, for each of *Haemonchus* (HC), *Moniezia* (Mon), Nematodirus (Nem), *Ostertagia* (Oster), and *Trichostrongylus* (Trich). The results are shown in Table 3, below:

| | | Performance | | | | | | | | | |
|---|---|---|---|---|---|---|---|---|---|---|---|
| | | HC | | Trich | | Nem | | Oster | | Mon | |
| Set | Method | Pre (%) | Rec (%) | Pre (%) | Rec (%) | Pre (%) | Rec (%) | Pre (%) | Rec (%) | Pre (%) | Rec (%) |
| 1 | CropFit | 88.7 | 85.9 | 81.8 | 84.4 | 96.5 | 100 | 91.94 | 89.06 | 100 | 90.6 |
|   | Template | 77.0 | 89.1 | 69.6 | 75.0 | 94.1 | 100 | 94.1 | 75 | 100 | 97.8 |
| 2 | CropFit | 92.9 | 82.8 | 85.5 | 92.5 | 96.5 | 100 | 93.4 | 89.1 | 100 | 95.31 |
|   | Template | 82.9 | 90.6 | 76.1 | 84.4 | 100 | 100 | 88.7 | 73.4 | 97.0 | 100 |
| 3 | CropFit | 91.4 | 82.8 | 82.4 | 87.5 | 100 | 98.4 | 92.0 | 89.1 | 98.3 | 92.2 |
|   | Template | 83.8 | 96.9 | 72.9 | 79.7 | 98.5 | 100 | 86.8 | 71.9 | 96.9 | 96.9 |

-continued

| | Performance | | | | | | | | | |
|---|---|---|---|---|---|---|---|---|---|---|
| | HC | | Trich | | Nem | | Oster | | Mon | |
| Set Method | Pre (%) | Rec (%) | Pre (%) | Rec (%) | Pre (%) | Rec (%) | Pre (%) | Rec (%) | Pre (%) | Rec (%) |

It will be noted that crop fit methods are generally superior.

Example 3: Comparison of Crop Fit and Template-Based Methods in the Identification of Individual Ova Versus Ova Clusters Performance of a detection algorithm using crop fit versus template-based methods was assessed, for each of *Haemonchus* (HC), *Moniezia* (Mon), Nematodirus (Nem), *Ostertagia* (Oster), and *Trichostrongylus* (Trich), where the ova are touching or non-touching. The results are shown in Table 4, below:

| | | Estimated Recall (Average) | | | | |
|---|---|---|---|---|---|---|
| Mode | Methods | HC | Trich | Nem | Oster | Mon |
| Touching | CropFit | 54.65 | 0 | N/A | N/A | N/A |
| | Template | 84.68 | 100 | N/A | N/A | N/A |
| Non-touching | CropFit | 66.79 | 50 | 100 | 100 | 50 |
| | Template | 95 | 62.5 | 100 | 75 | 83.3 |

It will be noted generally that where individual ova are concerned the crop fit method was superior to the template method, with the reverse being observed where the ova are touching.

While the invention has been disclosed in connection with the preferred embodiments shown and described in detail, various modifications and improvements thereon will become readily apparent to those skilled in the art.

Accordingly, the spirit and scope of the present invention is not to be limited by the foregoing examples, but is to be understood in the broadest sense allowable by law.

The invention claimed is:

1. A computer-implemented method for training a computer-implemented learning method to identify a genus or species of a parasite ovum in a sample, the method comprising:
   accessing a plurality of computer-readable training images, the training images being obtained by light microscopy of one or more samples containing a parasite ovum and a non-parasite ovum material;
   using a first subset of the plurality of computer-readable training images to perform human-supervised machine learning to distinguish images containing a parasite ovum from non-parasite ovum material to provide a machine learning model configured to distinguish parasite ovum material from non-parasite ovum material;
   using a second subset of the plurality of computer-readable training images to perform frame cropping, the frame cropping comprising identifying a parasite ovum and cropping one or more of the plurality of computer-readable training images so as to produce one or more cropped computer-readable images, each of the one or more cropped computer-readable images showing predominantly the parasite ovum;
   by human means identifying the genus or species of the parasite ovum in each of the one or more cropped computer-readable images where identification is possible;
   associating an identification label with each of the one or more cropped computer-readable images where identification was possible;
   applying a computer-implemented deep learning network feature extraction method to each labelled cropped computer-readable image; and
   applying the machine learning model to each cropped computer-readable image to determine if the cropped computer-readable image contains a parasite ovum,
   wherein the computer-implemented learning method is configured to associate one or more features extracted by the feature extraction method with a parasite ovum.

2. The computer-implemented method of claim 1, wherein the cropping of one or more of the plurality of computer-readable training images comprises distinguishing the parasite ovum from the microscopy field background and/or the non-parasite ovum material, and cropping the parasite ovum such that the image comprises predominantly or substantially only parasite ovum.

3. The computer-implemented method of claim 2, wherein the 1 distinguishing of the parasite ovum from the non-parasite ovum material is implemented at least in part by computer means.

4. The computer-implemented method of claim 3, wherein the distinguishing of the parasite ovum from the non-parasite ovum material is by human-assisted computer means.

5. The computer-implemented method of claim 4, wherein the human-assisted computer means comprises:
   dividing a computer-readable training image into a series of frames,
   by human means identifying the presence or absence of a parasite ovum in each of the series of frames,
   applying a computer-implemented feature extraction method to each of the series of frames, and
   applying a computer-implemented learning method to each of the series of frames,
   wherein the computer-implemented learning method is configured to associate one or more extracted features with the presence or absence of a parasite ovum in a frame.

6. The computer-implemented method of claim 5, wherein the association is used to identify the presence or absence of a parasite ovum in a plurality of frames that were not used in the human-assisted computer means, and where the parasite ovum is present cropping around the parasite ovum such that the image comprises predominantly or substantially only a parasite ovum.

7. The computer-implemented method of claim 1, wherein each of the cropped images and/or features extracted therefrom is/are stored in a computer-readable database in linked association with its respective identification label.

8. The method of claim 1, wherein the parasite ovum is the ovum of an intestinal parasite of a non-human animal.

9. The method of claim 1, wherein the parasite ovum is selected from *Haemonchus, Moniezia, Nematodirus, Ostertagia* and *Trichostrongulus*.

10. The method of claim 1 that is capable of training a computer to correctly identify parasite ova to the following levels of precision: ≥98.5% for *Haemonchus*, 100% for *Moniezia*, and 100% for Nematodirus.

* * * * *